US011774444B2

United States Patent
Ghiran et al.

(10) Patent No.: US 11,774,444 B2
(45) Date of Patent: Oct. 3, 2023

(54) DETECTION AND IDENTIFICATION OF CELL BOUND AND SOLUBLE ANTIGENS USING MAGNETIC LEVITATION

(71) Applicant: Beth Israel Deaconess Medical Center, Inc., Boston, MA (US)

(72) Inventors: Ionita C. Ghiran, Winchester, MA (US); Nathan Shapiro, Groton, MA (US); Anish V. Sharda, Brookline, MA (US); Edward J. Felton, Medfield, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 788 days.

(21) Appl. No.: 16/349,235

(22) PCT Filed: Nov. 10, 2017

(86) PCT No.: PCT/US2017/061048
§ 371 (c)(1),
(2) Date: May 10, 2019

(87) PCT Pub. No.: WO2018/089760
PCT Pub. Date: May 17, 2018

(65) Prior Publication Data
US 2019/0293639 A1    Sep. 26, 2019

Related U.S. Application Data

(60) Provisional application No. 62/421,151, filed on Nov. 11, 2016.

(51) Int. Cl.
*G01N 33/543* (2006.01)
*B03C 1/01* (2006.01)
(Continued)

(52) U.S. Cl.
CPC ......... *G01N 33/54326* (2013.01); *B03C 1/01* (2013.01); *B03C 1/0332* (2013.01);
(Continued)

(58) Field of Classification Search
CPC ......... G01N 33/54326; G01N 33/5044; G01N 33/537; G01N 33/56966; G01N 33/56972; G01N 35/0098; B03C 1/0332
See application file for complete search history.

(56) References Cited

U.S. PATENT DOCUMENTS

2010/0285606 A1* 11/2010 Phillips ............ G01N 33/54333
436/526
2015/0268234 A1* 9/2015 Whitesides .......... G01N 33/571
506/9
2016/0313332 A1 10/2016 Lee et al.

FOREIGN PATENT DOCUMENTS

WO    WO 2015/130913 A1    9/2015

OTHER PUBLICATIONS

Baday et al. Integrating cell phone imaging with magnetic levitation (i-LEV) for label-free blood analysis at the point-of-living. Small 12(9): 1222-1229 (Mar. 2, 2016).*
(Continued)

*Primary Examiner* — Gailene Gabel
(74) *Attorney, Agent, or Firm* — Wolf, Greenfield & Sacks, P.C.

(57) ABSTRACT

Methods and apparatus for detecting cell-bound and soluble antigens in a biological sample are described. The method comprises forming complexes of at least one antibody-coated bead and at least one antigen in a solution, placing the solution in a magnetic field such that the formed complexes levitate in the solution at a particular height, and determining at least one characteristic of the antigen in the complexes
(Continued)

based, at least in part, on an image of the complexes showing the magnetic levitation height.

20 Claims, 10 Drawing Sheets

(51) Int. Cl.
| | |
|---|---|
| B03C 1/033 | (2006.01) |
| B03C 1/30 | (2006.01) |
| B03C 1/32 | (2006.01) |
| G01N 9/36 | (2006.01) |
| G01N 33/50 | (2006.01) |
| G01N 35/00 | (2006.01) |
| G01N 33/569 | (2006.01) |
| G01N 33/537 | (2006.01) |

(52) U.S. Cl.
CPC .............. *B03C 1/30* (2013.01); *B03C 1/32* (2013.01); *G01N 9/36* (2013.01); *G01N 33/5005* (2013.01); *G01N 33/5044* (2013.01); *G01N 33/537* (2013.01); *G01N 33/56966* (2013.01); *G01N 33/56972* (2013.01); *G01N 35/0098* (2013.01); *B03C 2201/26* (2013.01)

(56) References Cited

OTHER PUBLICATIONS

PCT/US2017/061048, Jan. 19, 2018, International Search Report and Written Opinion.
PCT/US217/061048, May 23, 2019, International Preliminary Report on Patentability.
International Search Report and Written Opinion for International Application No. PCT/US2017/061048 dated Jan. 19, 2018.
International Preliminary Report on Patentability for International Application No. PCT/US2017/061048 dated May 23, 2019.
[No Author Listed], Global Tuberculosis Report 2015. Work Health Organization (WHO). 2015. 204 pages.
[No Author Listed], 90-90-90 An Ambitious Treatment Target to Help End the Aid Epidemic. (UNAIDS). TJUNPoHA. 2014. 40 pages.
Berg et al., Cellphone-Based Hand-Held Microplate Reader for Point-of-Care Testing of Enzyme-Linked Immunosorbent Assays. ACS Nano. 2015;9(8):7857-66.
Chen et al., Antibody CR1-2B11 recognizes a non-polymorphic epitope of human CR1 (CD35). Clin Exp Immunol. 2007;148(3):546-54.
Cockburn et al., Erythrocyte complement receptor 1 (CR1) expression level is not associated with polymorphisms in the promoter or 3' untranslated regions of the CR1 gene. Int J Immunogenet. 2006;33(1):17-20.
Cornacoff et al., Primate Erythrocyte-Immune Complex-Clearing Mechanism. J Clin Invest. 1983;71(2):236-47.
D'Ambrosio et al., Point-of-care quantification of blood-borne filarial parasites with a mobile phone microscope. Science Translational Medicine. 2015;7(286):1-10.
Durmus et al., Magnetic levitation of single cells. Proc Natl Acad Sci U S A. 2015;112(28):E3661-8.
Edris et al., Antibody therapy targeting the CD47 protein is effective in a model of aggressive metastatic leiomyosarcoma. Proc Natl Acad Sci U S A. 2012;109(17):6656-61.
Ghiran et al., Ligation of erythrocyte CR1 induces its clustering in complex with scaffolding protein FAP-1. Blood. 2008;112(8):3465-73.
Glodek et al., Ligation of complement receptor 1 increases erythrocyte membrane deformability. Blood. 2010;116(26):6063-71.
Holton et al., Initial assessment of the Pathogenic Mechanisms of the recently identified Alzheimer Risk Loci. Ann Hum Genet. 2013;77(2):85-105.
Kelly et al., The use of the enzyme-linked immunosorbent assay (ELISA) for the detection and quantification of specific antibody from cell cultures. Immunology. 1979;37(1):45-52.
Knowlton et al., Sickle cell detection using a smartphone. Scientific reports. 2015;5(15022):1-11.
Knowlton et al., Smart-Phone Based Magnetic Levitation for Measuring Densities. PLoS One. 2015;10(8):1-17.
Larcher et al., Expression of the C3d/EBV Receptor and of Other Cell Membrane Surface Markers Is Altered upon HIV-1 Infection of Myeloid, T, and B Cells. J Acquir Immune Defic Syndr. 1990;3(2):103-8.
Osaro et al., Rh isoimmunization in Sub-Saharan Africa indicates need for universal access to anti-RhD immunoglobulin and effective management of D-negative pregnancies. Int J Womens Health. 2010;2:429-37.
Peeling, Applying new technologies for diagnosing sexually transmitted infections in resource-poor settings. Sex Transm Infect. 2011;87 Suppl 2:ii28-30.
Petti et al., Laboratory Medicine in Africa: A Barrier to Effective Health Care. Clin Infect Dis. 2006;42(3):377-82.
Pirnstill et al., Malaria Diagnosis Using a Mobile Phone Polarized Microscope. Scientific Reports. 2015;5:1-13.
Sela-Culang et al., The structural basis of antibody-antigen recognition. Front Immunol. 2013;4(302):1-13.
Tassaneewan et al., A smartphone dongle for diagnosis of infectious diseases at the point of care. Science Translational Medicine. 2016;7(273):1-11.
Tham et al., Complement receptor 1 is the host erythrocyte receptor for Plasmodium falciparum PfRh4 invasion ligand. Proc Natl Acad Sci U S A. 2010;107(40):17327-32.
Bates et al., Investigating membrane protein dynamics in living cells. Biochem Cell Biol. Dec. 2006;84(6):825-831.
Ehrlich et al., Histology of the Blood: Normal and Pathological. Cambridge: Printed by J and C F Clay, at the University Press. Nature Publishing Group. Aug. 30, 1900: 1609(62):410-411.
Felton et al., Detection and quantification of subtle changes in red blood cell density using a cell phone. Lab Chip. Jul. 2016; 16: 3286-95.
Ghiran et al., The cytoplasmic tail of human erythrocyte CR1 (complement receptor 1) binds FAP-1, a scaffolding protein. Mol Immnol. Jun. 2004;41:235. Abstract.
Jacquier et al., Disulfide linkage between C3b and tetanus toxin on tetanus toxin-specific EBV-transformed B cells. J Immunol. May 15, 1993;150(10):4253-60.
Roberts et al., 2-Chloroadenosine inhibits complement-induced reactive oxygen metabolite production and recovery of human polymorphonuclear leukocytes attacked by complement. Biochem Biophys Res Comm. Jan. 31, 1985;126(2):692-7.
Rodbard et al., Kinetics of two-site immunoradiometric ('sandwich') assays-II. Studies on the nature of the 'high-dose hook effect'. Immunochemistry. Feb. 1978;15(2):77-82.
Svetic et al., A primary intestinal helminthic infection rapidly induces a gut-associated elevation of Th2-associated cytokines and IL-3. J Immunol. Apr. 15, 1993; 150(8 Pt 1):3434-41.
Thieblemont et al., Triggering of complement receptors CR1 (CD35) and CR3 (CD11b/CD18) induces nuclear translocation of NFkB (p50/p65) in human monocytes and enhances viral replication in HIV-infected monocytic cells. J Immunol. Nov. 15, 1995;155(10):4861-7.
Weber et al., Structural origins of high-affinity biotin binding to streptavidin. Science. Jan. 6, 1989;243(4887):85-8.

\* cited by examiner

DETECTION AND IDENTIFICATION OF CELL BOUND AND SOLUBLE ANTIGENS USING MAGNETIC LEVITATION

RELATED APPLICATIONS

This application is a national stage filing under 35 U.S.C. 371 of International Patent Application Serial No. PCT/US2017/061048, filed Nov. 10, 2017, which claims the benefit under 35 U.S.C. § 119(e) of U.S. Provisional Application No. 62/421,151, filed Nov. 11, 2016. The entire contents of these applications are incorporated by reference herein in their entireties.

GOVERNMENT SUPPORT

This invention was made with government support under National Institutes of Health Grant Nos. HL126497, TW09915, and HL096795. The government has certain rights in the invention.

BACKGROUND

The use of smartphones as medical diagnostic devices has emerged as a new imaging and analysis platform. Due to compactness and portability, ease of use, and relative low cost of components, smartphone-enabled, -assisted, or -controlled medical diagnostic devices are gaining popularity over dedicated stand-alone technology, particularly for use in resource-poor settings as point-of-care (POC) devices. Numerous smartphone-based tests are now in existence, such as smartphone-controlled ELISA for diagnosis of HIV and syphilis, smartphone microscopy of parasites such as malaria, Helminths and tuberculosis, smartphone-based nucleotide detection systems, etc. As a result, World Health Organization and various NGO groups have increasingly promoted the development and testing of these medical diagnostic tests.

SUMMARY

Some embodiments are directed to a magnetic levitation-based technique for measurement of mass and density of living cells by detecting membrane-bound and soluble antigens using antibody-coated beads. The basis of this approach is translation of antigen-antibody binding events that lead to the formation of bead-cell complexes and alteration of the levitation height when placed in a magnetic field. Techniques described in accordance with some embodiments do not require any background subtraction operations, and can provide results in as little as five minutes. By using capture beads of different colors, shapes or densities, at least some of the techniques described herein can be multiplexed to interrogate a blood sample for more than one virus or one soluble or membrane-bound antigen. Some embodiments that implement the assay described herein can be used both in laboratory as well as point-of-care (POC) settings, providing binary as well as quantitative measurements without the need for sophisticated scientific equipment or dedicated training.

Some embodiments are directed to a portable point-of-care (POC) device configured to perform magnetic levitation. The portable POC device includes a magnetic levitation module configured to generate a magnetic field within which a container containing a mixture of antibody-coated beads and cells may be placed, an imaging system configured to image at least a portion of the container placed in the magnetic levitation system, and a processing system configured to process one or more images acquired by the imaging system.

Some embodiments are directed to a magnetic levitation device configured to be coupled to a microscope. The magnetic levitation device is configured to generate a magnetic field within which a container containing a mixture of antibody-coated beads and cells may be placed.

Some embodiments are directed to a method of detecting antigens in a biological sample using magnetic levitation, wherein the method comprises creating a mixture of antibody-coated beads and cells having membrane-bound antigens, incubating the mixture to facilitate the formation of bead-cell complexes, placing the mixture having the bead-cell complexes into a magnetic field, and detecting the presence or absence of the antigen in the mixture based, at least in part, on magnetic levitation properties of the components of the mixture.

Some embodiments are directed to a method of detecting eosinophil antigens by magnetic levitation.

Some embodiments are directed to a method of detecting CD8(+) T cell-specific antigens by magnetic levitation.

Some embodiments are directed to a method of detecting red cell-bound antigens by magnetic levitation.

Some embodiments are directed to a method of detecting a virus bound to a complement receptor on a red blood cell by magnetic levitation.

Some embodiments are directed to a method of detecting soluble antigens by magnetic levitation.

Some embodiments are direct to a method of processing an image acquired using magnetic levitation to detect antigens bound to antibody-coated beads in a complex, wherein the method comprises determining a magnetic levitation height of the complex relative to the magnetic levitation height of other substances in the image.

Some embodiments are directed to a method of detecting lipids, proteins and nucleic acids (DNA, RNA species), either soluble, cell bound or membrane-bound, present in biological fluids, such as blood, urine, cerebrospinal fluid, amniotic fluid, semen, etc. or cell cultures supernatants.

Some embodiments are directed to a method of detecting extracellular vesicles, ribonucleic protein complexes, lipoprotein complexes, or protein complexes present in biological fluids.

The foregoing summary is provided by way of illustration and is not intended to be limiting.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings:

FIGS. 1A-1E, shows a magnetic levitation setup and the how average density affects magnetic levitation in accordance with some embodiments, of which FIG. 1A shows a microscope placed on its side to capture images of a capillary tube containing a mixture of antibody-coated beads and cells having membrane-bound antigens; FIG. 1B illustrates a magnetic levitation setup showing top and bottom magnets with a capillary tube mounted on adjustable stages; FIG. 1C schematically shows a capillary tube mounted between two magnets; FIG. 1D shows an example of binding events with different densities; and FIG. 1E schematically shows an illustration of the example of FIG. 1D;

FIGS. 2A-2I, shows results of an experiment to detect Eosinophil and CD8(+) T cells-specific antigens by magnetic levitation in accordance with some embodiments, of which FIG. 2A shows a schematic drawing of binding between a capture bead and cell; FIG. 2B shows a magnetic levitation image of anti-IgG control beads in a PBMC solution, and a Gaussian fit of a bitmap of the magnetic levitation image; FIG. 2C shows flow cytometric analysis of mIgG control treated lymphocytes; FIG. 2D shows a magnetic levitation image of CD3 antibody treated beads in a PBMC solution, and a Gaussian fit of a bitmap of the magnetic levitation image; FIG. 2E shows flow cytometry of anti-CD3 treated cells; FIG. 2F shows a magnetic levitation image of Siglec-8 antibody treated beads with a binding of an eosinophil granulocyte enlarged in a marked area, and a Gaussian fit of a bitmap of the magnetic levitation image; FIG. 2G shows flow cytometry of anti-Siglec-8 treated beads; FIG. 2H shows a magnetic levitation image of a negative control arm indicating no BCC formation, and a Gaussian fit of a bitmap of the magnetic levitation image; and FIG. 2I shows flow cytometry of an eosinophil mIgG control;

FIGS. 3A-3I, shows results of an experiment to detect red cell-bound antigens by magnetic levitation in accordance with some embodiments, of which FIG. 3A is a schematic drawing of how a primary-, secondary antibody and antigen creates a bead-RBC complex; FIG. 3B shows a magnetic levitation image of a low CR1 level, and a corresponding bitmap analysis; FIG. 3C shows flow cytometry of a low CR1 level; FIG. 3D shows a magnetic levitation image of a high CR1 level, and a corresponding bitmap analysis; FIG. 3E shows flow cytometry of a high CR1 level; FIG. 3F shows a magnetic levitation image of 1:100 spikes Rh(+)-cells in Rh(−)-cells with Rh-antibody coated-beads and (Rh+) red blood cells, and a corresponding bitmap analysis; FIG. 3G shows a magnetic levitation image of IgG-beads in Rh+ washed blood, and a corresponding bitmap analysis; FIG. 3H shows a magnetic levitation image of anti-CD47-beads and red blood cells, and a corresponding bitmap analysis; and FIG. 3I shows a magnetic levitation image of IgG-beads in washed blood, and a corresponding bitmap analysis;

FIGS. 4A-4E, shows results of an experiment to detect a virus bound to CR1 on a red blood cell by magnetic levitation in accordance with some embodiments, of which FIG. 4A is a schematic drawing of EBV bound to CR1, detected with anti-EBV; FIG. 4B shows a magnetic levitation image of red blood cells with IgG-beads, and a corresponding bitmap analysis; FIG. 4C shows a magnetic levitation image of red blood cells with EBV antibody coated-beads, and a corresponding bitmap analysis; FIG. 4D shows, on the left side, a bright field microscopy image of RBCs and, on the right side, enlargements to a portion of the left-side image, of which the top-left enlargement shows a bright field image of the portion (DIC-technique), the top-right enlargement is the portion under fluorescence, the bottom-left enlargement is a FITC image, and the bottom-right enlargement shows a Brightfield+TxRed+FITC image; and FIG. 4E shows flow cytometry of negative and positive EBV;

FIGS. 5A-5C, shows results of an experiment to detect soluble antigens by magnetic levitation in accordance with some embodiments, of which of which FIG. 5A is a schematic drawing of an interaction between a goat anti-mouse bead and PMMA beads with polyclonal anti-BSA; FIG. 5B is a line graph showing a relationship between number of intermediate BBCs (Y-axis) and concentration of BSA (X-axis); and FIG. 5C shows magnetic levitation images and corresponding bitmap analyses at various concentrations (ng/mL) of soluble antigen;

FIG. 6A shows a device for performing magnetic levitation and imaging in accordance with some embodiments, and FIG. 6B shows parts of the device of FIG. 6A;

FIG. 6C shows bright-field images obtained using the device shown in FIG. 6A;

FIGS. 7A-7G show results of experiments in which different antigens were identified using magnetic levitation in accordance with some embodiments, of which FIG. 7A shows magnetic levitation images and corresponding bitmap analyses for CD3; FIG. 7B shows magnetic levitation images and corresponding bitmap analyses for Siglec-8; FIG. 7C shows magnetic levitation images and corresponding bitmap analyses for CD8; FIG. 7D shows magnetic levitation images and corresponding bitmap analyses for CD35/CR1; FIG. 7E shows magnetic levitation images and corresponding bitmap analyses for Rhesus; FIG. 7F shows magnetic levitation images and corresponding bitmap analyses for CD47; and FIG. 7G shows magnetic levitation images and corresponding bitmap analyses for EBV;

DETAILED DESCRIPTION

Figure 1:
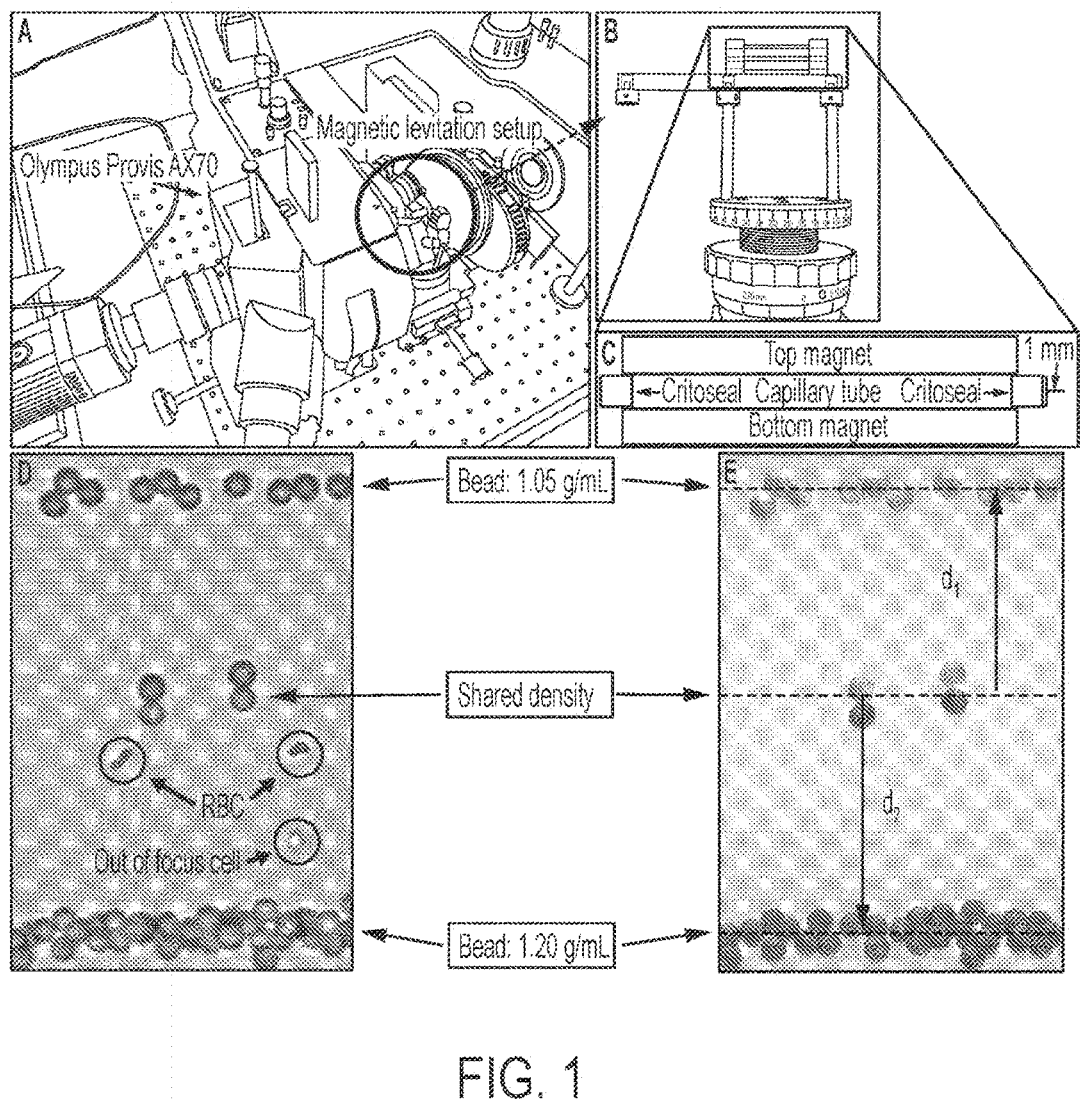
FIG. 1, which includes

Magnetic levitation-based and smartphone-adapted techniques that measure the specific mass and density of individual red blood cells (RBCs) by reporting the levitation height of cells as compared to a set of density reference beads have been previously described. Those techniques provide for rapid separation and identification of old, new, iron-deficient, and sickled red blood cells. Digital image acquisition using a smartphone camera provided a rapid, portable and inexpensive generation of quantifiable output using unprocessed or minimally processed blood. The measured signal was generated by a change in the levitation height of cells that was indicative either of their activation status, in case of neutrophils, hemoglobin or water content in the case of red blood cells, or density in the case of circulating tumor cells.

Current detection methods in biomedical sciences are based on translating specific binding events, such as antibody-antigen interactions, into easy-to-detect, linear signals. The signals are based either on light (fluorescence, bioluminescence, chemiluminescence), color or color shift (colorimetric) of the probes, or changes in the radioactivity, electrical or light scattering properties of the targets. These methods usually require specialized detection instrumentation tuned specifically to the readout method, often involving complex assays that are difficult to employ in resource-poor settings.

Some embodiments are directed to a novel, density-based magnetic levitation method for the identification of cell-bound antigens, named "Magnetic-Linked Immunosorbent Assay", or MeLISSA. Although cells are described herein as the substrate to which antigens are bound, it should be appreciated that the techniques described herein may be used to identify and/or quantify any substrate having a membrane to which one or more antigens may be detected.

Accordingly, although antigens may be described herein as "cell-bound" in some embodiments, antigens bound to a membrane of another type of biological entity including, but not limited to, proteins, viruses, cytokines (e.g., chemokines), and bacteria may be detected.

The techniques described herein allow for detection of soluble and cell-bound antigens using a readout output of a shift in the levitation height of cells or bead-cell complexes (BCC) that are easily imaged and analyzed using a microscope or mobile device. The control or antigen-specific antibodies are linked, depending on the assay, to one or two reference beads, with densities different than those of the interrogated cells. Following the interaction between the antibody-coated beads and the target antigen, the resulting complexes levitate at predictable and measurable heights, away from the non-interacting beads and cells. The target antigen, therefore, can be specifically detected based solely on the altered density and levitation level upon binding to the detection bead. When combined with a mobile camera with WiFi, Bluetooth, or other communication capabilities, the device may serve as a replacement for more sophisticated methods, such as flow cytometry, ELISA, or western blotting to be used in low-resource environments as a tool for screening, detection and quantification of various blood antigens and pathogens. In some of the experiments described in more detail below, the interrogated cells include eosinophils and T cells. However, it should be appreciated that the techniques described herein may be used with any cell type present in blood as well as circulating tumor cells, and circulating fetal cells based on cell surface markers.

Detection of Soluble and Membrane-Bound Antigens

In accordance with various aspects of some embodiments, experiments were conducted to evaluate the ability of the techniques described herein for detecting and/or identifying soluble and membrane-bound antigens using magnetic levitation. Below is a description of the experimental details.

Materials and Methods

Antibodies: anti-Siglec-8 (Biolegend, San Diego, Ca); mouse anti-human CD3 (Biolegend, San Diego, Ca); CR1: anti-CD35 (Bio-Rad, Hercules, Calif.); mouse anti-Human anti-RhD (Abcam, Cambridge, Mass.); anti-human CD47 (BD Biosciences Pharmingen, Franklin Lakes, N.J.); anti-EBV antibody (kind gift from Dr. Gordon Ogembo, University of Massachusetts, Mass., USA). Mouse IgG, whole molecule (Jackson ImmunoResearch Labs, West Grove, Pa., USA)

Preparation of Red Blood Cells

The study was approved by the Beth Israel Deaconess Medical Center Institutional Review Board. Ten to 20 μL of fresh whole blood were obtained via finger prick from healthy volunteers. Cells were washed twice and re-suspended in HBSS with calcium and magnesium (HBSS$^{++}$) to a final concentration of $5 \times 10^7$ cells/mL, and used within 1 hour.

Preparation of Peripheral Blood Mononuclear Cells and Polymorphonuclear Cells

Ten mL of whole blood was drawn in syringes prefilled with 2.3 mL of 6% Dextran 500 (Sigma-Aldrich, St. Louis, Mo.) and 1 mL of 3.2% Sodium Citrate (Sigma-Aldrich, St. Louis, Mo.). After gently mixing the blood by tapping, the syringe rested in an upright position for 45 minutes. The RBC-free fraction was layered above 15 mL of Ficoll-Paque PREMIUM (density 1.077 g/mL, GE Healthcare Bio-Sciences) in a 50 mL tube and centrifuged at 500×g for 10 minutes. The peripheral blood mononuclear cells (PBMC) were located at the plasma-Ficoll interface, and neutrophils at the bottom of the tube along with unlyzed RBCs. The PBMC layer was collected and set aside for CD3 experiments. The polymorphonuclear cells (PMN) were resuspended in 0.5 mL of HBSS$^{--}$ and transferred to a new 50 mL tube. Contaminating RBCs were lyzed using hypotonic lysis. Twenty mL of 0.2% sodium-chloride (NaCl) were added to the PMN pellet for 45 seconds, followed by 20 mL of 1.6% NaCl. The cells were centrifuged at 500×g for 10 minutes after the lysing and the pellet was resuspended in 1.0 mL of HBSS$^{--}$. After isolation, PBMC and PMNs were washed twice and re-suspended in HBSS' to a final concentration of $5 \times 10^7$ cells/mL.

Antibodies Coupling

Two sterile Eppendorf microcentrifuge tubes were filled with 400 μl PBS and 100 μl goat anti-mouse IgG beads with a density of 1.05 g/ml (goat anti-mouse IgG-coated particles, 5.0% w/v, Spherotech) while on ice. The control and the target antibody were added to separate tubes to a final concentration of 2 μg/ml each. The bead-antibody solutions were then incubated for 30 minutes at 37° C. and washed twice in 1 mL PBS. The pellet was resuspended in 100 μl PBS and prepared in 40 mM of gadobenate dimeglumine solution (MultiHance, Bracco Diagnostics, Monroe Township, N.J.) (500 mM Gadolinium (Gd$^{3+}$) stock solution). The prepared cell suspensions were incubated for 30 minutes at room temperature, loaded in between the two magnets and viewed under the microscope.

Detection of Soluble Antigens

Polymethylmethacrylate microspheres (PMMA beads) were diluted in compound 2-(N-morpholino) ethanesulfonic acid (MES) buffer and incubated with 1-ethyl-3-(3-dimethylaminopropyl) carbodiimide hydrochloride (EDC) for 20 minutes at room temperature. The beads were then coated with 6 m/ml anti-BSA and re-suspended in PBS buffer. Anti-BSA were also attached onto goat anti-mouse beads using the same method as described before to a concentration of 2 μg/ml. BSA was incubated with the high density PMMA beads for 30 minutes at 37° C. at a concentration of 0.5 ng/ml, 0.1 ng/ml, 0.05 ng/ml, 0.01 ng/ml and control without BSA. The beads were then washed twice and incubated with the bottom PMMA beads for 30 minutes at 37° C. The samples were analyzed after being resuspended in 100 mM Gd$^+$ with HBSS" as buffer.

Magnetic Levitation

Cells (concentration $5 \times 10^7$ cells/mL) suspended in HBSS' or HBSS$^{--}$ (for eosinophil granulocytes only) were mixed with gadolinium (Gd$^{3+}$). Cells were levitated in a final 40 mM Gd solution for all the experiments involving cells. The Goat anti-mouse IgG(FC) Particles mixed with cells were diluted 1:200. The levitation was performed in square capillary tubes with the dimensions, 1×1 mm cross section, and 5 cm in length (VitroCom, Mountain Lakes, N.J.). Critoseal (Fisher Scientific, Pittsburgh, Pa.) applied to the ends prior to loading to prevent drifting of cells during imaging. N52-grade NdFeb magnets with dimensions 1×5× 50 mm (KM Magnetics, Pipersvelle, Pa.) positioned with the poles facing each other were used, repelling one another with a 1 mm distance in between (FIG. 1C). The magnets had a surface field of 0.375 T. In some embodiments, permanent magnets having other desired magnetic properties may be selected, for example, based on the magnetic characteristics of the biological structure(s) being interrogated.

Microscopy Setup

An Olympus Provis AX-70 microscope mounted on the side as depicted in FIG. 1A was used to capture images in side-view of the capillary tube. With this setting, the gravitational, magnetic and buoyant forces accountable for the levitation of the cells were appropriate aligned. In order to adjust for the length and the vertical orientation of the capillary tube with respect to the objective and focus while maintaining proper Kohler illumination, micromanipulation X-Y and Z-stages were used (Thorlabs, Newton, N.J.)(FIG. 1.B). This setup enabled imaging of levitating cells and beads using medium-high magnification objectives such as 40×0.70 NA and 60×0.70 NA. Most of the images were acquired using the 10×0.30 NA or 20×0.45 NA to allow the recording and analysis of large number of cells in one frame. Images were acquired using a QImaging Retiga EXi Blue cooled CCD camera controlled by Image-Pro Plus 7.0 (Media Cybernetics, Inc., Rockville, Md.), 15 minutes after inserting the capillary tube between the magnets.

Image and Statistical Analysis

Images captured were cropped to only show beads, cells and intermediate bead-cell complexes (BCC). The 16 bit .tiff files were inverted and binarized, such that black was assigned 0 value, and white 1. The bitmaps were exported to Excel (Microsoft, Redmond, Wash.), where an auto-sum was performed for each column of pixels. Waves were created in Igor Pro (Wavemetrics, Portland, Oreg.). Gaussian fits were performed for all the peaks. Next, the area under the Gaussian fit corresponding to the BCC was calculated in the XY table of the Gaussian fit, the X value increased in uniform increments. Since the area under the curve is $\int f(x)dx$, dx (the increment) is constant and f(x) is the Y value, the expression became (increment)*$\Sigma_{x_i}^{x_f} f(x)$. The borders $x_f$ and $x_i$ of the peak were at each end of the peak and represented the unbound beads and cells respectively. The distance between the peaks was calculated from the midpoints of each Gaussian fits. The peak shift, indicative of bead: cell or bead: bead complexes, was computed by measuring the difference between each adjacent peaks. Unpaired, t-test was used to determine if the difference between various populations was significant.

Flow Cytometry

Cells, isolated as described above, were incubated for 30 min at 37° with corresponding primary antibodies, washed and re-suspended in HBSS$^{++}$. Cells were then labeled using AlexaFluor 488 conjugate Goat anti-mouse IgG (H+L) for an additional 15 mins, at room temperature, washed twice, resuspended in buffer, and analyzed on a FacsScan flow cytometer within 10 minutes from the last wash step. Results were then analyzed using Flowjo 10.1r5 software (Tree Star).

Mini-MeLISSA

A Yi Action Camera, Full HD 1080p videos, 16 MP photos, was used a base for the portable device. The original objective lens of the camera was removed and replaced with a high NA (0.72) aspheric lens (Edmund Optics, Barrington, N.J.), identical with the lens using for the microscope-attached setup shown in FIG. 1. The frame for the camera was designed in Adobe Illustrator (Adobe Systems Incorporated, San Jose, Calif.), and parts were cut on a laser cutter as shown in FIGS. 5A and 5B. The magnets used were identical to those used for the microscope setup. The camera contained a Wi-Fi communication capability and the broadcasted images were able to be viewed/captured in real-time on a device with a Wi-Fi connection and access to an application store. A separate LED module was installed in front of the camera to prevent the dependence of the image acquisition on the ambient light. Images were captured via the App YI action for this experiment on an iPhone 6.

Magnetic Levitation Focuses Objects Based on Density

FIG. 1, which includes FIGS. 1A-1E, shows a magnetic levitation setup and the concept of average density in accordance with some embodiments. FIG. 1A shows an Olympus Provis AX70 microscope placed on its side to capture the images of a capillary tube containing a mixture of antibody-coated beads and cells having membrane-bound antigens. The microscope has three micro-manipulators, giving the ability to search the whole capillary tube in both horizontally and vertically, and to focus the levitating objects. Critoseal was used to seal the capillary tube. FIG. 1B illustrates the magnetic levitation setup showing the top and bottom magnet with the capillary tube mounted on adjustable stages. FIG. 1C shows a schematic of the capillary tube mounted between two magnets. FIG. 1D shows detection of binding events with different densities. The magnetic levitation image of FIG. 1D shows that capture of beads spiked with a minimum number of cells for size comparison. Upon cell-bead interaction, a bead-bead complex levitated between the high and low density beads. FIG. 1E shows a schematic illustration of the image in FIG. 1D to describe the concept of magnetic levitation and density.

Magnetic levitation focuses objects with different densities at specific heights following a non-linear relationship between magnetic field density, concentration of gadolinium solution, density of the objects and their paramagnetic properties. In a given setup, objects with negligible magnetic properties rest at a levitation height that depends exclusively on the object density. The levitation height of a complex of two beads with different densities depends on their resulting average density. As shown in FIG. 1D, the two interacting beads that levitated between the top and bottom rows of beads had an average density of 1.125 g/mL due to the fact that both beads had the same diameters (10 μm), thus the same volumes, and densities of 1.05 and 1.2 g/mL, respectively. Therefore, the final levitation height of the bead complexes was located directly between the top and bottom bead. In addition, the magnetic levitation setup was sensitive enough to detect density gradients within the levitating objects, as shown in FIGS. 1D and 1E, where beads with higher density always pointed downward and beads with lower density upward. This principle was used to detect and visualize specific binding events between antibody-coated beads and cell-bound and soluble antigens as a POC-friendly alternative to microscopy, flow cytometry and ELISA.

Experiment 1: Magnetic Levitation Detects Antigens on White Blood Cells

Figure 2:
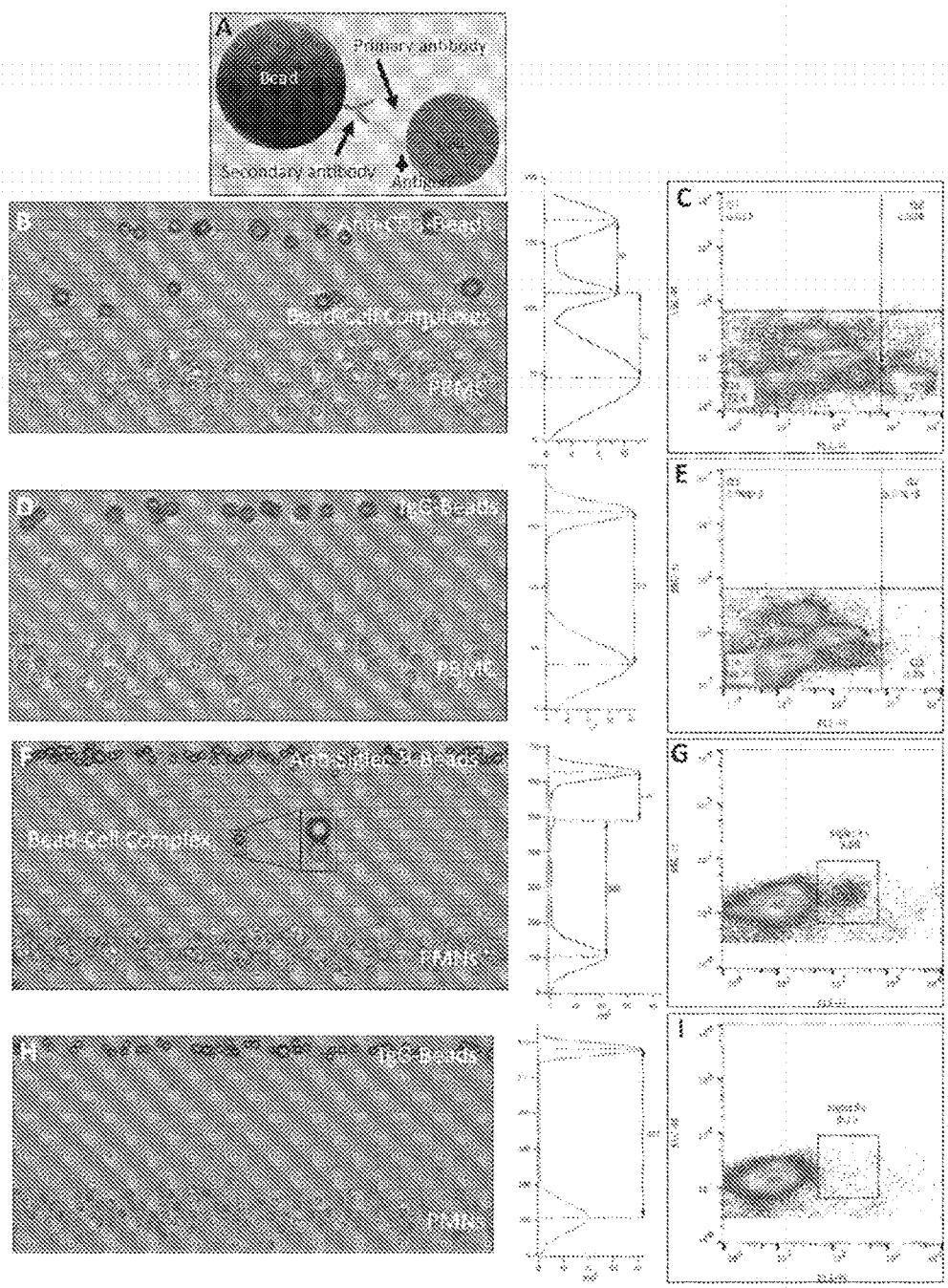
FIG. 2, which includes

To evaluate the ability of magnetic levitation to detect different antigens on the surface of white blood cells (WBC), PBMC and PMC from buffy coat from blood collected from self-declared healthy donors was isolated. Both an abundant WBC, the T-cell, and a relatively scarce WBC, the eosinophil granulocyte were detected (see FIG. 2, which includes FIGS. 2A-2I).

A schematic drawing of binding between a capture bead and cell is shown in FIG. 2A. FIG. 2B shows magnetic levitation of anti-IgG control beads in a PBMC solution showing the absence of bead-cell complexes. On the right (applies for all magnetic levitation images): Gaussian fit from the bitmap analysis. The Gaussian fit is performed for the whole image. FIG. 2D shows magnetic levitation of CD3 antibody treated beads in a PBMC solution, which shows binding of CD3 positive T-cells. Primary antibodies were attached to capture antibody-coated beads following the protocols described above. CD3+ T-cells were detected by magnetic levitation using anti-CD3 (FIG. 2B) in the PBMC layer compared to the IgG control (FIG. 2D). An area under the curve technique, as shown on the graphs located on the right side of each microscopy images, was used to analyze the results. The peak between the beads and cells rows, shown in FIG. 2B, represents the bead-cell complexes. In the control arm of the experiment, PBMC were incubated with control IgG-coated beads and showed no discernable binding between cells and beads.

Flow cytometry analysis performed in parallel confirmed a second population of cells with a higher fluorescence (MFI=130, 27.4% of population—FIG. 2C) than that of the IgG control (MFI=21.6, 0.29% of population—FIG. 2E). FIG. 2C shows flow cytometric analysis of the mIgG control treated lymphocytes showing the background binding (0.29% cell in the positive gate). PMN cells were treated with FC gamma-Receptor blocker. FIG. 2E shows flow cytometry of the anti-CD3 treated cells with FL1, SSC, which shows a subpopulation of 27.4% cells.

FIG. 2F shows magnetic levitation (cropped image horizontally) of Siglec-8 antibody treated beads with a binding of an eosinophil granulocyte enlarged in the marked area. FIG. 2G shows flow cytometry of the anti-Siglec-8 (4 µg/ml) treated beads showing a subpopulation (3.00%) of Siglec-8 positive cells (eosinophil granulocytes). FIG. 2H shows magnetic levitation of the negative control arm of the experiment showing no BCC formation. PBMC cells are treated with FC-Receptor blocker. FIG. 2I shows flow cytometry of the eosinophil mIgG control showing background binding of 0.29%.

To test a lower detection limit of this approach, a cell type, the eosinophil granulocyte, that makes up only 2-3% of a healthy donors nucleated blood cells, and are therefore considered relatively rare compared to other white blood cells was chosen for detection. FIG. 2F, shows the presence of eosinophils bound to anti-Siglec-8-coated beads, and lack of binding in the control arm of the experiment (FIG. 2H). On average, 3-4 BCC were identified in one full capillary tube containing beads coated with anti-Siglec-8, while no BCC were observed in the control tube. Moreover, the eosinophil-specific granules were clearly visible, further confirming the specificity of the binding of anti-Siglec-8 coated beads. The flow cytometry results shown in FIGS. 2G and 2I, also confirm the specific identification of eosinophil population by siglec-8 (MFI=9.75, 3.0% of total event) vs IgG-control (MFI=7.25, 0.29% of total events).

To test the ability of the magnetic levitation-based capture assay described herein in accordance with some embodiments to identify specific cells by cell surface markers, a biotin/streptavidin-based system was used (FIGS. 7A-7G). It was found that the approach generated significant background, thus rendering the biotin-streptavidin system unsuitable for detection of low abundant events. With the approach described herein, the efficiency of binding and identifying of eosinophils was around 10-20%, judging by the number of eosinophils identified compared to their expected number in the PBMC population present in a capillary tube. Manipulation of the cells during loading and the short time of incubation with antibody-coated beads may explain the observed sensitivity of detection. Increasing detection efficiency may be possible by altering the protocol.

Experiment 2: Detection of Membrane-Bound Antigens on Red Blood Cells

Figure 3:
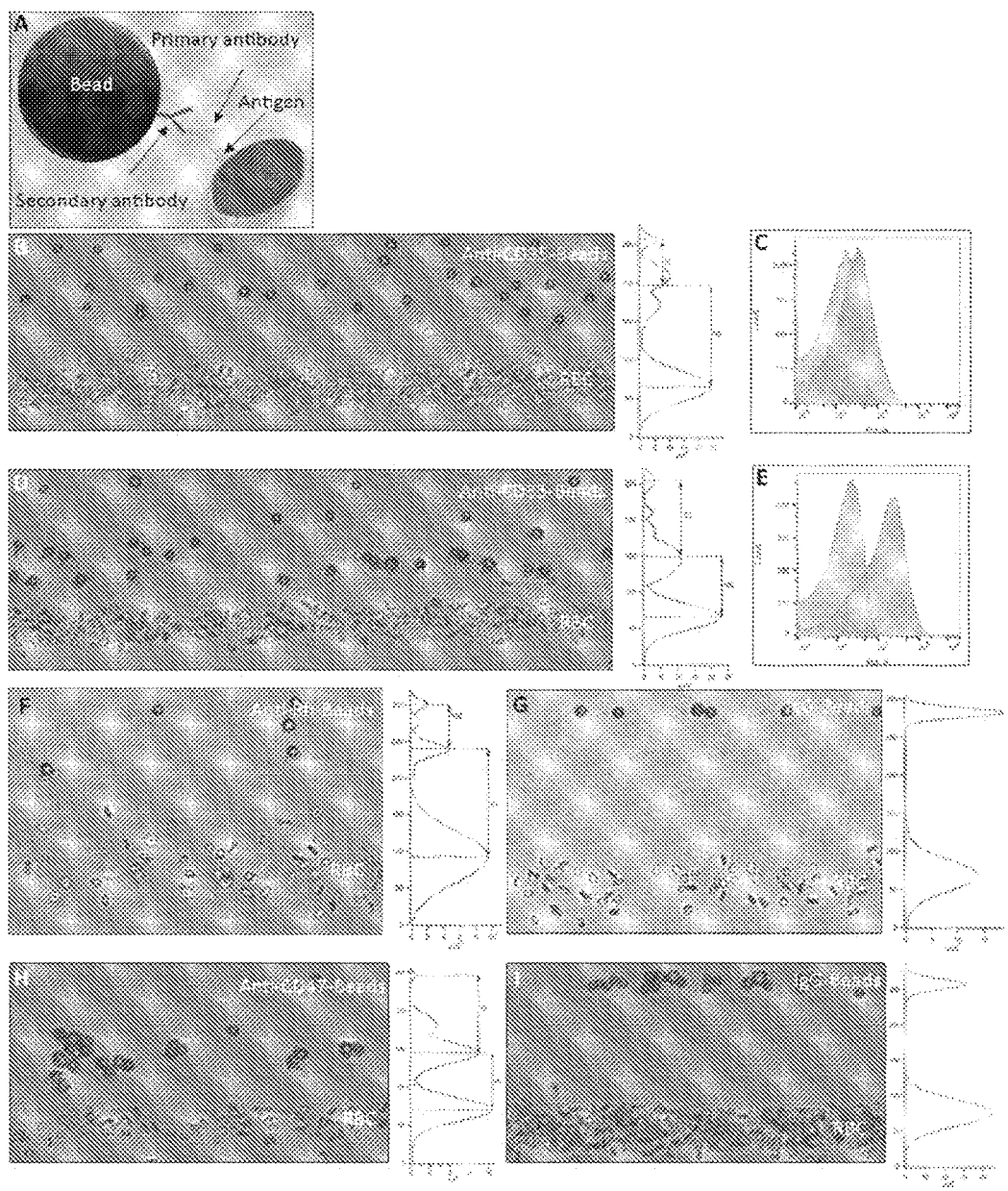
FIG. 3, which includes

It was also investigated whether magnetic levitation could identify not just the presence, but also distinguish between various expression levels of cell surface antigens. CR1 (CD35, complement receptor 1), an exclusively human protein, which is expressed on circulating red blood cells (RBC) in a genetically determined fashion, with individuals expressing either 90 CR1 copies/RBC, 500 CR1/RBC, or 1200 CR1/RBC was chosen as the cell-surface antigen. Individuals expressing high levels of CR1 on RBC membranes, are protected against late-onset Alzheimer's disease and septic shock, while low CR1 expressers are protected against malaria, as CR1 serves as docking protein for *Plasmodium falciparum*. RBCs from previously-identified low and high CR1-expressers were incubated with beads coated with anti-CR1 or IgG control (see FIG. 3, which includes FIGS. 3A-3I).

The overall approach for this experiment is shown schematically in FIG. 3A, which shows a schematic drawing of how the primary-, secondary antibody and antigen creates the bead-RBC complex. FIG. 3B shows magnetic levitation of low CR1 level (90 molecules/RBC) with attached bitmap analysis. Beads were treated with CD35 (CR1) antibody. FIG. 3D shows magnetic levitation of high CR1 level (1200 molecules/RBC) with attached bitmap analysis. Beads were treated with CD35 (CR1) antibody. The results illustrated in FIGS. 3B and D show that a high CR1 expression level promoted an increase in the number of RBCs per anti-CR1-coated bead interaction, compared to low CR1 expression. Moreover, in the high CR1/RBC samples, the BCC were not only larger, but also levitated at a lower level when compared to the BCC from low CR1/RBC expressers, signifying higher densities of these complexes due to the presence of more RBCs/BCC. The peaks, representing the average distance between the capture beads and unbound beads confirm the observed results, with a Y-peak value of 88.8 [83.0; 95.5] for high CR1, and only 58.5 [58.0; 59.0] with a P=0.002 and a 95%-confidence interval [18.2; 42.3].

The magnetic levitation results were compared to flow cytometry, a method currently accepted and widely used for detection of expression levels of cell surface markers. FIG. 3C shows flow cytometry of low CR1 level. Blue is mIgG control and red is anti-CD35. FIG. 3E shows flow cytometry of high CR1 level. Blue is mIgG control and red is anti-CD35. Results in FIGS. 3C and 3E, show the relative shifts in fluorescence for low and high CR1 expression as detected by flow, that followed the same pattern as the one observed by MeLISSA.

Rapid detection of circulating RBCs with unique antigenic signatures, such as Rh(+) in Rh(−) pregnant woman, are beneficial in POC settings for early detection of high risk pregnancies. The sensitivity of approach described herein was tested to identify Rh(+) RBCs spiked in an Rh(−) blood sample. RBCs from a known Rh+healthy donor were mixed with RBC from a Rh(−) donor at a 1:100 ratio for 5 minutes and then incubated with either anti-RhD-coated or IgG control beads. The results are shown in FIGS. 3F and 3G. FIG. 3F shows magnetic levitation of 1:100 spikes Rh(+)-cells in Rh(−)-cells with Rh-antibody coated-beads and (Rh+) red blood cells showing binding of RBC with beads. FIG. 3G shows magnetic levitation of IgG-beads in Rh+ washed blood, showing no bead-cell complexes. FIGS. 3F and 3G show that the histogram profile of the control only shows two peaks, one corresponding to the beads and other to RBCs, in the experimental arm there was a significant population in between the two reference peaks, indicative of BCC formation. Although the number of RhD molecules per RBC is in the range of 10,000 to 30,000, significantly more than the number of CR1 from high expressers, the number of Rh(+) RBCs captured was lower, and the size of BCC smaller compared to those seen with RBC from high CR1 expressers. One explanation for this apparent discrepancy could be that the number of available Rh (+) RBCs for cell-bead interaction in the spiked samples was low, thus preventing the formation of large BCC. Therefore, it was tested whether a large number of antigenic determinants on the cell surface would negatively impact the imaging or analysis efficiency. Detection of CD47, a critical molecule involved in blocking the phagocytosis of RBCs during the immune transfer process was compared by interacting with its cognate receptor on tissue macrophages, SIRP-alpha. The expression level of CD47 on human circulating RBCs is approximately 50,000 molecules/RBC.

FIGS. 3H and 3I show that the highly abundant CD47 generated large BCC complexes, which could be challenging from a data processing and analysis stand point. In particular, FIG. 3H shows magnetic levitation of anti-CD47-beads and red blood cells showing binding of RBC with beads and FIG. 3I shows magnetic levitation of IgG-beads in washed blood, showing no bead-cell complexes. Lowering of the concentration of detection antibody immobilized on capture beads, and/or decreasing the number of target cells would lower the binding efficiency between the beads and the cells, thus overcoming the aforementioned limitations. Similar to other detection methods such as, ELISA or flow cytometry, it is necessary to have previous knowledge of the antigen density, presentation, and availability on the cell membrane, as well as specific antibody affinity.

Experiment 3: MeLISSA can Detect Cell-Bound Viruses in Circulation

Figure 4:
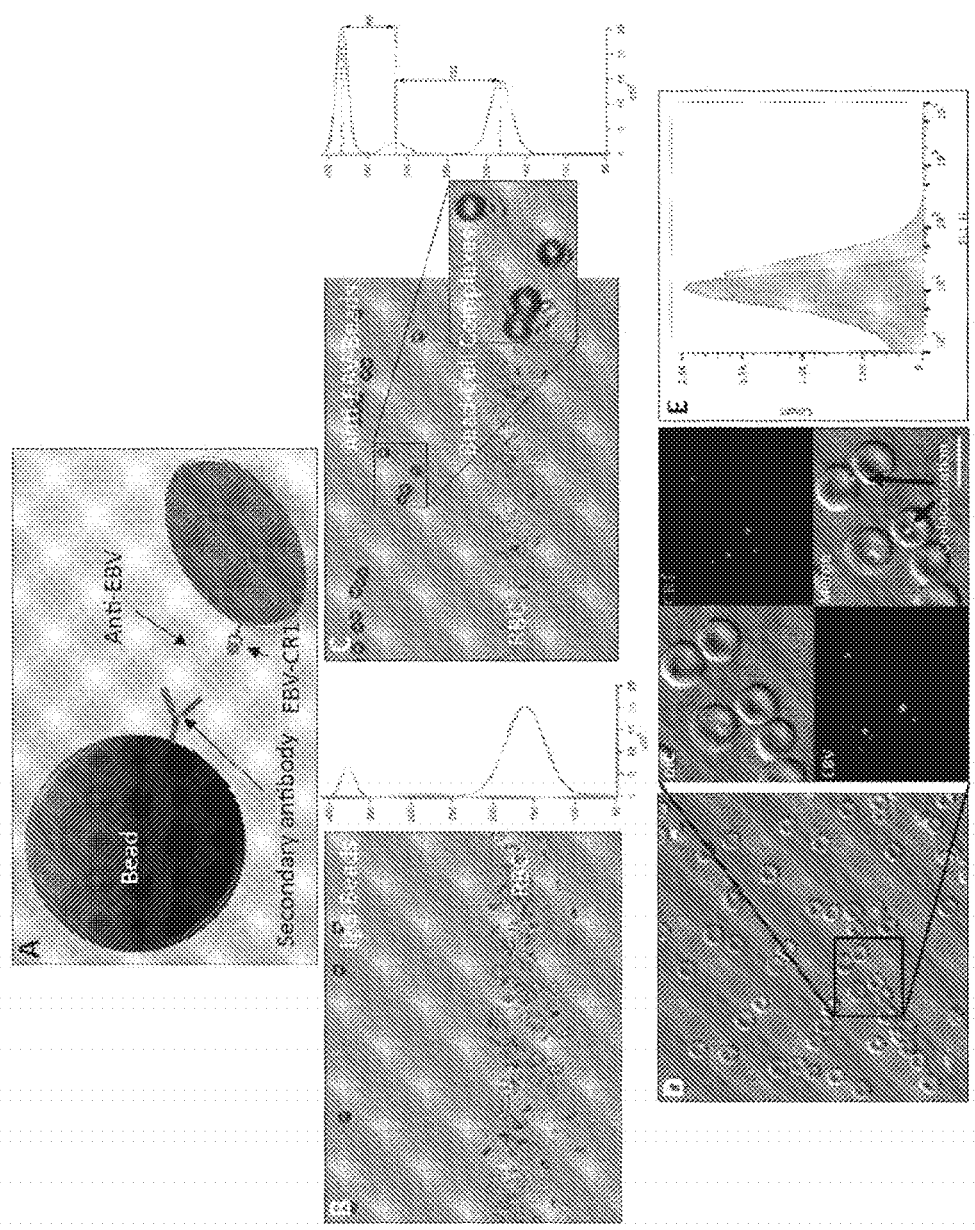
FIG. 4, which includes

In humans, circulating RBCs continuously clear blood pathogens and foreign particles by transferring them to the reticulo-endothelial system through a process called immune-adherence clearance. During early stages of an infection, most viral (HIV, EBV, Dengue, Zika, Chikungunya, HAV, HBV) and bacterial pathogens become opsonized with complement components C3b, C4b, MBL, and then circulate for days bound to RBCs, using RBC CR1 as the docking protein. It was tested whether the approach used in the experiments described above would allow the detection of RBC CR1-bound virions (see FIG. 4, which includes FIGS. 4A-4E). FIG. 4A shows a schematic drawing of EBV bound to CR1, detected with anti-EBV in accordance with some embodiments.

FIG. 4B shows magnetic levitation of red blood cells with IgG-beads, showing no binding and FIG. 4C shows magnetic levitation of red blood cells with EBV antibody coated-beads, showing binding interaction in the enlarged image. FIGS. 4B and 4C show that incubation of RBCs isolated from an Epstein-Barr virus (EBV) positive donor with anti-EBV beads, formed BCC, whereas incubation of RBCs isolated from non-infected donors with the same beads generated no detectable binding events.

These results were confirmed both by using immunofluorescence microscopy and flow cytometry. The EBV genome was labeled using Syto16, a nucleic acid specific fluorescent dye (Ex 488 nm/Em 519 nm), and RBC CR1 was labeled by incubating RBCs with an anti-CR1 reporter antibody followed by Alexa 594-labeled secondary antibody. The left frame of FIG. 4D is a bright field microscopy of RBCs. The enlarged image to the right of FIG. 4D shows a bright field image of the enlarged square (DIC-technique). The upper right image of FIG. 4D is under fluorescence revealing TxRed showing CR1. The lower left image of FIG. 4D shows FITC showing EBV. The lower right image shows a Brightfield+ TxRed+FITC image. Arrows are shown as pointing towards yellow, co-localization points. The white line represents 25 micro meters. FIG. 4D shows a differential interference contrast (DIC)/Nomarski image of one of the RBC fields investigated, with the inset focusing on the cellular location of CR1 molecules (red), EBV virions (green) and co-localization between the CR1 and EBV (yellow). The lack of complete co-localization between CR1 and EBV signals may be due to the fact that some circulating EBV virions lack genetic material (empty virion) thus being Syto16 negative, while some CR1 molecules may already be occupied by immune complexes, therefore inaccessible to EBV virions, but accessible to the reporter anti-CR1 antibody.

FIG. 4E shows flow cytometry of negative (red) and positive (blue) EBV showing a right skewed tail and a slight shift. The flow cytometry analysis of RBCs isolated from a EBV position donor show a small shift in fluorescence signal (MFI=14.7) compared to control IgG (MFI=7.4) confirming the presence of EBV on the circulating RBCs. The results of this experiment demonstrate that MeLISSA can readily detect RBC bound virus particles, simply by incubating antibody-coated beads with whole blood and detecting the presence of newly formed BCC.

Experiment 4: MeLISSA Detects the Presence of Soluble Antigens

Figure 5:
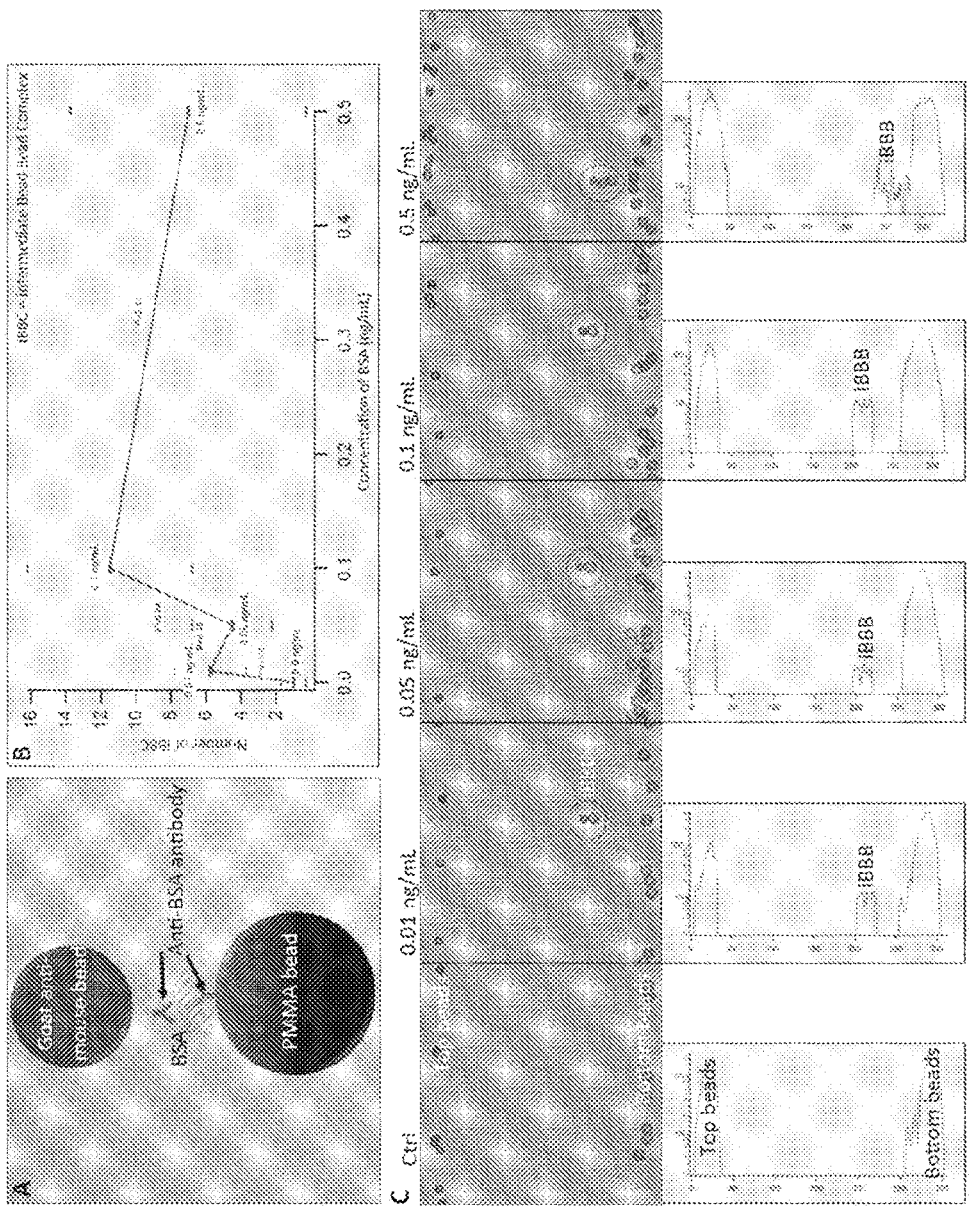
FIG. 5, which includes

The ability of MeLISSA to detect soluble antigens was tested as shown in FIG. 5, which includes FIGS. 5A-5C. FIG. 5A shows a schematic drawing of interaction between the goat anti-mouse bead and PMMA beads with polyclonal anti-BSA. In this approach, the antibody-coated high density beads (1.2 g/mL) should bind to the antibody-coated low-density beads (1.05 g/mL) by a bridge formed by the target antigen, thus generating a bead-bead complex of intermediate density. Two sets of beads with densities of 1.05 and 1.2 g/mL, each coated with 1 g/mL of anti-bovine serum albumin (BSA) polyclonal antibody were used. Beads were incubated with increasing concentrations of BSA from 0.01 to 0.5 ng/mL for 30 minutes a 37° C. temperature, followed by magnetic levitation for 10 minutes.

FIG. 5B shows a line graph showing the number of intermediate BBCs on Y-axis and concentration of BSA on X-axis. Unpaired T-test was performed between each of the points: 0.0-0.01 P=0.02, 0.01-0.05 P=0.44, 0.05-0.1 P=0.001 and 0.1-0.5 P=0.14. FIG. 5C shows from right to left: Control (Ctrl) with no BSA showing no intermediate bead-bead-bindings (iBBC) in the entire length of the capillary. No clustering factor of bottom beads (top picture captured on the big microscope (MeLISSA) with bitmap analysis beneath with a log-scale on Y-axis). 0.01 ng/mL BSA showing 1 iBBC. Low clustering factor of bottom beads. 0.05 ng/mL BSA showing 1 iBBC. Intermediate clustering factor of bottom beads. 0.1 ng/mL BSA showing 1 iBBC. Intermediate-high clustering factor of bottom beads. 0.5 ng/mL BSA showing 1 iBBC. High clustering factor of bottom beads.

The results illustrated in FIG. 5B show that while the control samples contain none or few intermediate bead-bead complexes (iBBC) (1+/−0.71/capillary tube, FIG. 5C), in the experimental arm there were increasing number of bead-bead complexes as the concentration of soluble antigen increased from 0.01 ng/mL to 0.1 ng/mL; 0.01 (P=0.005, 95%-CI=[2.1; 7.4]), 0.05 (P=0.03, 95%-CI=[0.6; 6.4]) and 0.1 (P=0.005, 95%-CI=[4.7; 16.3]). The high-density beads (1.2 g/mL) were attached to the low-density beads (1.05 g/mL) by a bridge formed by the target antigen, BSA in this case. Besides looking at the detection of soluble antigen versus control, the probability was examined quantifiably as it is with an ELISA. As seen in FIG. 5B there was a significant difference between 0.01 ng/mL and 0.1 ng/mL (1.51+/−4.7/capillary tube, FIG. 5C) and also between 0.05 ng/mL (4.5+/−2.3/capillary tube, FIG. 5C) and 0.1 ng/ml BSA (P=0.01). However, no difference was observed between 0.01 ng/mL and 0.05 ng/mL (P=0.44). With a concentration of 0.5 ng/mL BSA, there were large discrepancies in results, so large that they are not even significant versus the control (P=0.13, 95%-CI=[−2.2; 14.2]), which may be due to residual BSA being present after the 2 washes before the second incubation with the high intensity beads rather than being due to saturation or steric hindrance.

Because the high-density beads were incubated first with the BSA, some homologues BBCs in this row was expected. The low-density bead clusters lack these clusters because the BSA was removed in the first wash step. Because of this, the clustering of the high-density beads (beads/cluster) was included as an additional factor in quantification of antigen detection efficiency. The trend shown on the graph suggests proportionality at lower concentrations 0 ng/mL to 0.1 ng/mL, but more experiments may be necessary to smooth out the discrepancies.

Figure 6:
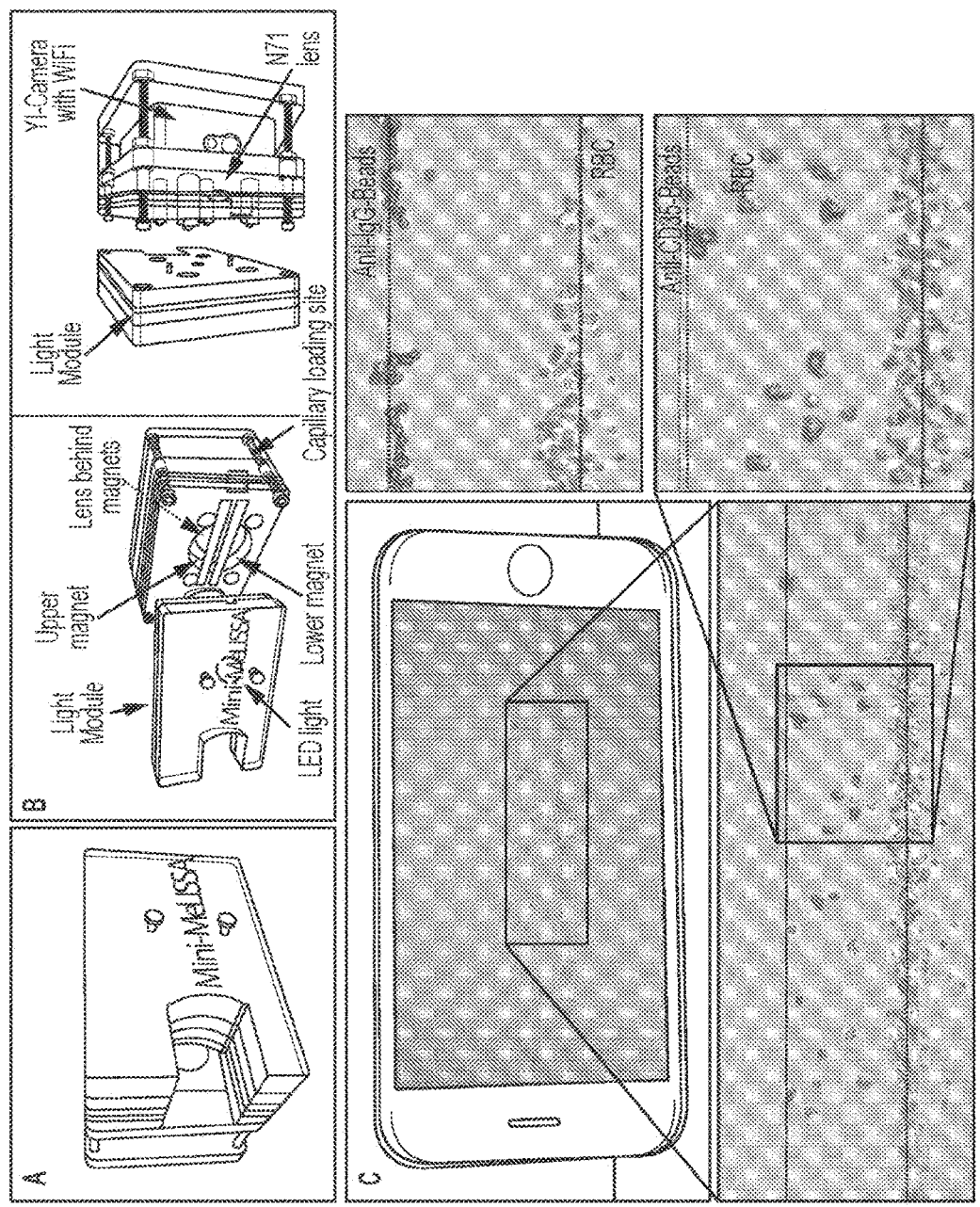
FIG. 6 includes FIGS. 6A-6C.
Figure 7A:
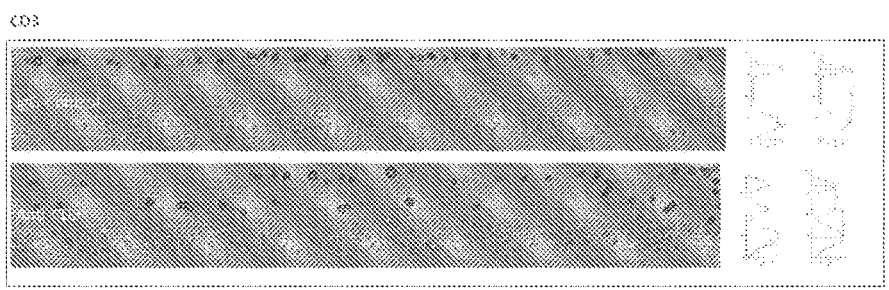
Figure 7B:
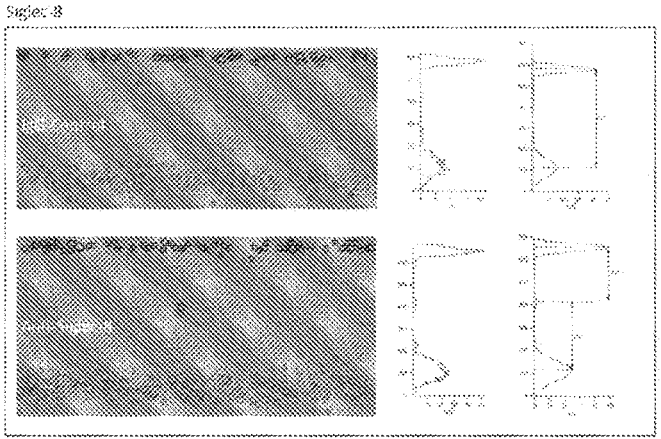
Figure 7C:
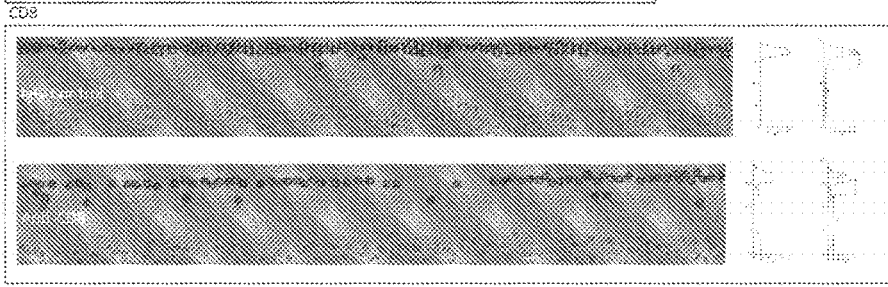
Figure 7D:
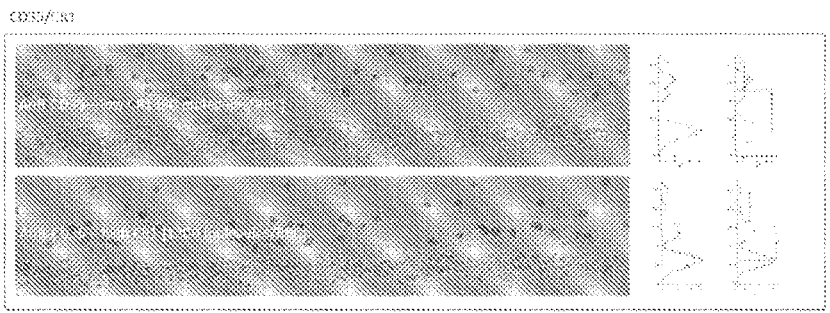
Figure 7E:
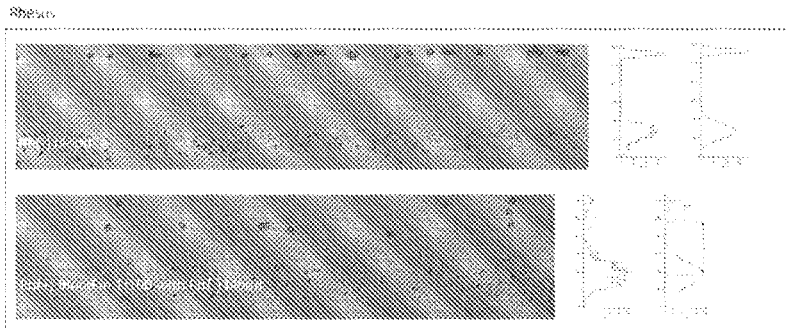
Figure 7F:
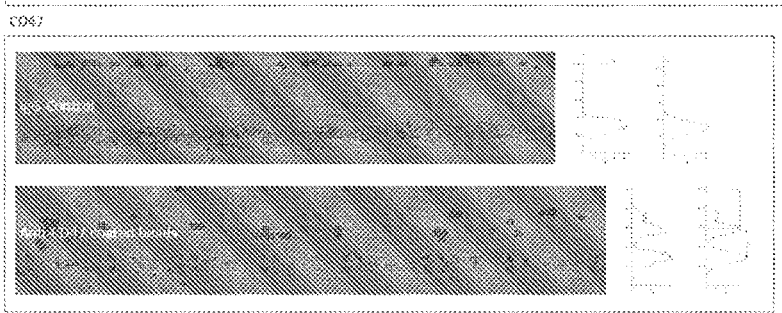
Figure 7G:
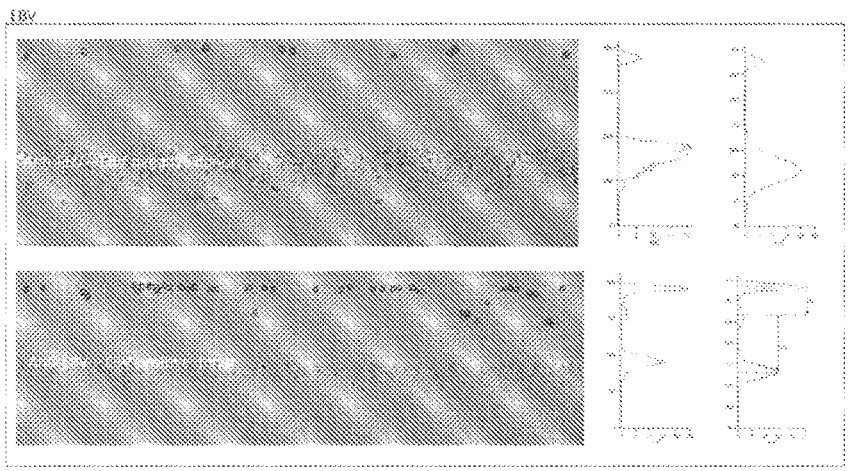

Mini-MeLISSA Produces Images Similar to Those Obtained Using a Standard Microscope There is need for low-cost POC assays in resource-poor settings that are easy to operate and inexpensive to maintain. While employing a cell phone would be very advantageous for imaging, data collection and analysis, the adaptor necessary to connect the diagnostic device to the phone would likely be brand and model specific. Some embodiments are directed to an apparatus called "mini-MeLISSA," which is an inexpensive camera that is compact and sturdy, captures images with a simple manual focus comparable to the quality of a laboratory microscope, and broadcasts it to any smartphone or tablet in the vicinity from its built-in WiFi (or other communications technology). FIG. 6, which includes FIGS. 6A-6C, illustrates an embodiments of an exemplary mini-MeLISSA device and its parts (FIGS. 6A and 6B) and an image broadcasted to a smartphone (FIG. 6C) using the its own WiFi signal. More specifically, FIG. 6A shows a compact mini-MeLISSA device with a YI-camera. The left side of FIG. 6B shows a deconstructed Mini-MeLISSA device, showing two module pieces. The left is the light module, which has a built-in LED light running on 2.5 V, 0.018 A. The right is the camera shell module, housing the WiFi-based Camera and the magnetic levitation setup with the two magnets, and room for a squared 1×1 mm capillary tube. The specialized lens is placed right behind the magnets. The focus is a fixed focus calibrated with thin slices of acrylics and plastics. Right: Upper-side-view of the two-piece module showing the light module to the left and the camera frame with camera on the right. The camera is held together by friction between the plates fixed with screws. Black acrylic is used to block natural light.

FIG. 6C shows a smartphone image of a bright field image taken with the Mini-MeLISSA device of FIG. 6A. The enhanced below image shows anti-CD35-beads attached to CR1 on RBCs and enhanced further to the right. The donor was a high CR1 expresser. In the upper right corner is an enlarged image from the same donor, using IgG control beads, which shows no RBC:bead-binding events. Anti-CR1 beads were used to demonstrate the resolution of the YI-camera, which, using a single lens with an NA of 0.71, was able to detect BCC as well as the number of RBCs and detection beads for each cluster (insets). In some embodiments, mini-MeLISSA extends the portability of the magnetic levitation techniques described herein by providing a true POC-assay available for use in resource-poor settings.

Figure 8:
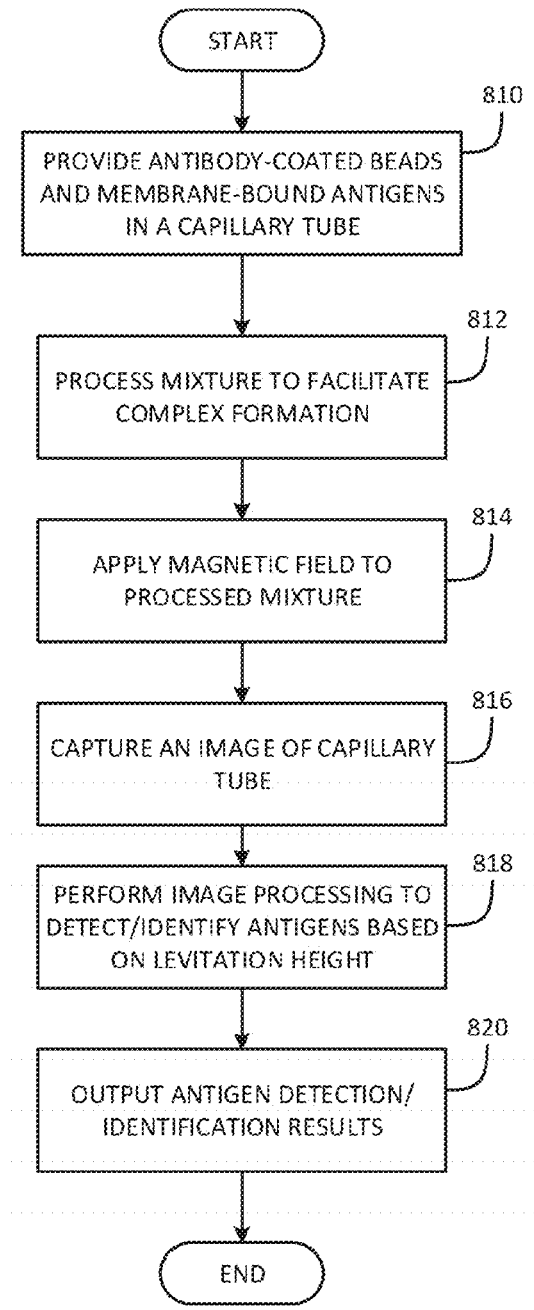
FIG. 8 illustrates a process for detecting/identifying antigens in a biological substance using magnetic levitation in accordance with some embodiments.

FIG. 8 illustrates a process for detecting and/or identifying membrane-bound antigens in accordance with some embodiments. In act 810, antibody-coated beads are provided along with cells or other biological structures (e.g., proteins, cytokines, viruses) having a membrane to which antigens may be bound. In some embodiments, the membrane-bound antigens may be included in blood, urine or another biological substance acquired from a human. The acquired biological specimen may be processed to separate particular types of cells to be combined with the antibody-coated beads in a capillary tube or other suitable container for processing in accordance with some embodiments. The process then proceeds to act 812, where the mixture of antibody-coated beads and cells having membrane-bound antigens is processed to facilitate the formation of complexes due to the binding of the antibodies of the antibody-coated beads and the membrane-bound antigens, if present. An suitable process may be used to facilitate complex formation including, but not limited to, incubation.

Following formation of bead-cell complexes, the process proceeds to act 814, where the processed mixture is placed in a magnetic field. Applying a magnetic field to the mixture causes separation between the beads and the cells in the capillary tube based on their different densities. Any bead-cell complexes formed in the mixture will levitate to a position in the capillary tube between the position of the beads and the cells due to the density of the complexes. For example, one or more cells having a membrane-bound antigen may form a complex with one or more antibody-coated beads. The density of the complex may be greater than that of the antibody-coated beads causing the complex to levitate at a lower position in the capillary tube than the position of the beads in the presence of a magnetic field.

The process then proceeds to act 816, where one or more images of at least a portion of the capillary tube are captured. The image(s) may be captured by a microscope, the camera in a smartphone or other electronic device, or any other type of camera. The process then proceeds to act 818, where image processing is performed on the image(s) to determine one or more of the presence of antigens, an identification of antigens, and a concentration of antigens in the sample. In some embodiments, the processing is performed based, at least in part, on the levitation height of complexes formed in the sample relative to the levitation position of the cells and beads.

The process then proceeds to act 820, where the results of the image processing are output. For example, in some embodiments, an identification of a type of one or more detected antigens may be displayed on a smartphone or other electronic device having a display. In some embodiments, the output may include an image of the capillary tube showing the detected antigen(s), a confidence score associated with the detection/identification result, a concentration of the detected antigen(s), or any combination of the foregoing to inform a user about the contents of the tested biological substance.

Figure 9:
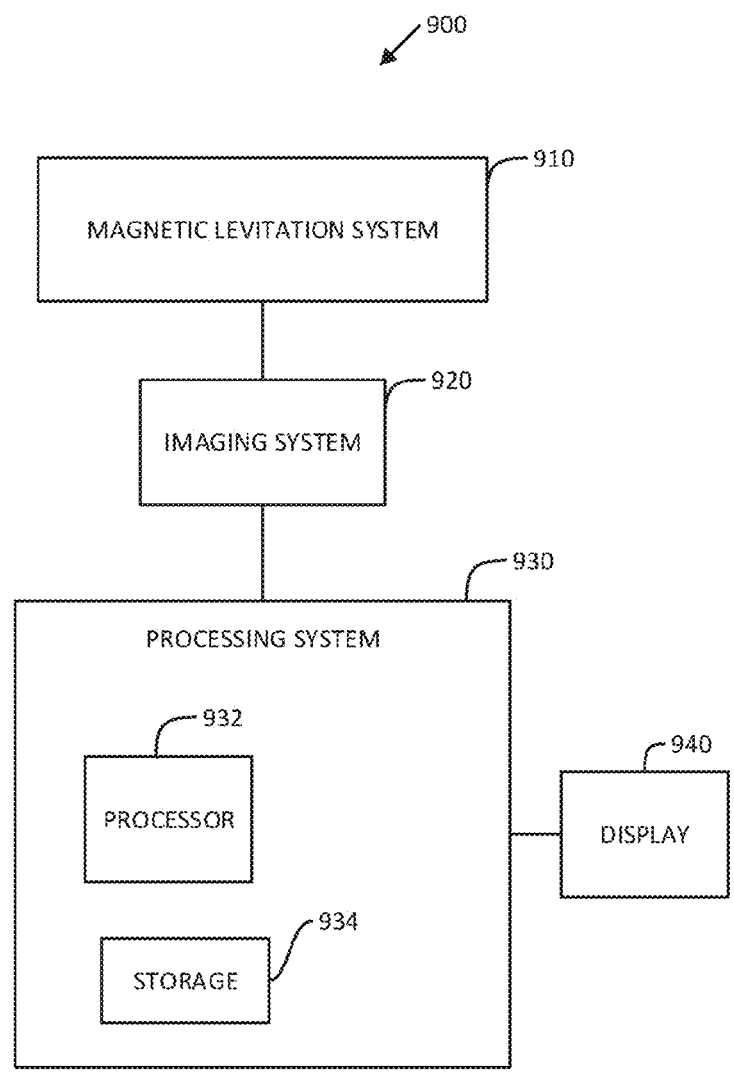
FIG. 9 shows a schematic of a block diagram of a system including components for performing an antigen detection/identification process in accordance with some embodiments.

FIG. 9 illustrates an example system 900 within which one or more of antigen detection techniques described herein may be implemented. System 900 includes magnetic levitation system 910 configured to generate a magnetic field within which a container (e.g., a capillary tube) containing a mixture of antibody-coated beads and cells (or other biological structures capable of having membrane-bound antigens) may be placed.

System 900 also includes imaging system 920 configured to image at least a portion of the container placed in the magnetic levitation system. In some embodiments imaging system 920 may be implemented as a microscope to which the magnetic levitation system 910 is coupled. In other embodiments, imaging system 920 may be implemented as a portable imaging system, such a camera on a smartphone, that may be reversibly coupled to magnetic levitation system 910 to capture an image. In yet further embodiments, imaging system 920 may be integrated with a portable magnetic levitation system 910 such that the portable magnetic levitation system itself may include the ability to capture images without the need to couple an external camera.

System 900 also includes processing system 930. Processing system 930 includes a processor 932 configured to process images received by the processing system and storage 934 configured to store unprocessed images, processed images, results of the image processing, or any combination of the foregoing. For example, in some embodiments, storage 934 is configured to store information about magnetic levitation heights for each of a plurality of antigens. In some embodiments, processor 932 performs imaging processing to determine one or more of a levitation height of complexes formed in the image, the presence/absence of formed complexes, an identification of one or more antigens, a concentration of one or more antigens, and a confidence score associated with a determination. In some embodiments, the determination may be made based, at least in part, on information stored in storage 934.

In some embodiments, imaging system 920 and processing system 930 are incorporated into a same device (e.g., a smartphone). In other embodiments, imaging system 920 and processing are coupled over one or more wired or wireless networks. For example, an image captured by imaging system 920 may be transmitted to processing system 930 for analysis over a WiFi connection, Bluetooth connection or any other suitable wired or wireless communication connection.

System 900 also includes display 940 configured to display information output from processing system 930. In some embodiments, display 940 is integrated with one or both of imaging system 920 and processing system 930, for example in smartphone. In other embodiments, display 940 may be communicatively coupled to processing system using one or more wired or wireless networks.

Various aspects of the apparatus and techniques described herein may be used alone, in combination, or in a variety of arrangements not specifically discussed in the embodiments described in the foregoing description and is therefore not limited in its application to the details and arrangement of components set forth in the foregoing description or illustrated in the drawings. For example, aspects described in one embodiment may be combined in any manner with aspects described in other embodiments.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be considered as one or more controllers that control the above-discussed functions.

In this respect, it should be appreciated that one implementation of the embodiments of the present invention comprises at least one non-transitory computer-readable storage medium (e.g., a computer memory, a USB drive, a flash memory, a compact disk, a tape, etc.) encoded with a computer program (i.e., a plurality of instructions), which, when executed on a processor, performs the above-discussed functions of the embodiments. The computer-readable storage medium can be transportable such that the program stored thereon can be loaded onto any computer resource to implement the aspects of the present invention discussed herein. In addition, it should be appreciated that the reference to a computer program which, when executed, performs the above-discussed functions, is not limited to an application program running on a host computer. Rather, the term computer program is used herein to reference any type of computer code (e.g., software or microcode) that can be employed to program a processor to implement the above-discussed aspects of the present invention.

Various aspects of the present invention may be used alone, in combination, or in a variety of arrangements not specifically discussed in the embodiments described in the foregoing and are therefore not limited in their application to the details and arrangement of components set forth in the foregoing description or illustrated in the drawings. For example, aspects described in one embodiment may be combined in any manner with aspects described in other embodiments.

Also, embodiments of the invention may be implemented as one or more methods, of which an example has been provided. The acts performed as part of the method(s) may be ordered in any suitable way. Accordingly, embodiments may be constructed in which acts are performed in an order different than illustrated, which may include performing some acts simultaneously, even though shown as sequential acts in illustrative embodiments.

Use of ordinal terms such as "first," "second," "third," etc. to modify elements does not by itself connote any priority, precedence, or order of one element over another or the temporal order in which acts of a method are performed. Such terms are used merely as labels to distinguish one element having a certain name from another element having a same name (but for use of the ordinal term).

The phraseology and terminology used herein is for the purpose of description and should not be regarded as limiting. The use of "including," "comprising," "having," "containing", "involving", and variations thereof, is meant to encompass the items listed thereafter and additional items.

Having described several embodiments of the invention in detail, various modifications and improvements will readily occur to those skilled in the art. Such modifications and improvements are intended to be within the spirit and scope of the invention. Accordingly, the foregoing description is by way of example only, and is not intended as limiting.

The invention claimed is:

1. A detection device for detecting and identifying an antigen in a biological sample using magnetic levitation, the device comprising:
   a magnetic levitation apparatus including:
      a pair of magnets configured to generate a magnetic field;
      a container holder arranged between the pair of magnets;
      a container containing a solution comprising antibody-coated beads configured to attach to target cell-bound antigens in the biological sample when the biological sample is added to the solution in the container, the solution and the biological sample forming a mixture, wherein, when the container is positioned in the container holder such that the mixture is exposed to the magnetic field generated by the pair of magnets, bead-cell complexes formed between the antibody-coated beads and the target cell-bound antigens in the biological sample magnetically levitate within the container; and an imaging device coupled to the magnetic levitation apparatus and configured to capture at least one image of the bead-cell complexes in the mixture and to identify the target cell-bound antigen when the mixture is present in the magnetic field of the magnetic levitation apparatus.

2. The device of claim 1, further comprising:
an imaging system configured to image the mixture in the container positioned in the container holder.

3. The device of claim 2, wherein the imaging system comprises a microscope arranged to capture at least one image of the mixture in the container.

4. The device of claim 3, wherein the microscope comprises a camera configured to capture at least one magnified image of the mixture in the container.

5. The device of claim 3, further comprising:
a processing system including a computer processor configured to process the at least one image captured by the imaging system to make a determination about components of the mixture in the container, wherein the determination is selected from the group consisting of:
measuring at least one levitation height of the bead-cell complexes in the mixture,
detecting a presence or an absence of the bead-cell complexes in the mixture,
determining an antigen identification of one or more cell-bound antigens in the mixture, and
determining a concentration of one or more cell-bound antigens in the mixture.

6. The device of claim 5, wherein the computer processor is further configured to determine a confidence score associated with the determination about components of the mixture in the container.

7. The device of claim 5,
wherein the processing system further includes a storage device configured to store information about magnetic levitation heights of each antigen of the one or more cell-bound antigens identified in the mixture, and
wherein the computer processor is configured to make a determination about the components of the mixture in the container based, at least in part, on the stored information.

8. The device of claim 5, wherein the determination about the components of the mixture comprises determining a levitation height of the bead-cell complexes in the mixture relative to a levitation height of at least one substance in the mixture that is not the bead-cell complexes in the mixture.

9. The device of claim 5, wherein the computer processor is further configured to process the at least one image by performing a statistical analysis of pixels in the at least one image captured by the imaging system.

10. The device of claim 2, wherein the imaging system comprises a camera of a mobile electronic device configured to be removably coupled to the magnetic levitation apparatus.

11. The device of claim 10, wherein the mobile electronic device comprises a smartphone.

12. The device of claim 1, wherein the biological sample comprises red blood cells, and wherein the target cell-bound antigens comprise red blood cell-bound antigens.

13. The device of claim 1, wherein the biological sample comprises white blood cells, and wherein the target cell-bound antigens comprise white blood cell-bound eosinophil antigens and/or CD8(+) T cell-bound antigens.

14. The device of claim 1, wherein the container comprises a capillary tube.

15. The device of claim 1, wherein each of the magnets in the pair of magnets is a permanent magnet.

16. The device of claim 1, wherein a surface field of each of the magnets in the pair of magnets is approximately 0.375 Tesla.

17. A portable point of care (POC) device configured to perform magnetic levitation to detect a presence of an antigen, the portable POC device comprising:
a magnetic levitation apparatus including:
a pair of magnets configured to generate a magnetic field,
a container holder arranged between the pair of magnets, and
a container containing a solution comprising antibody-coated beads,
wherein:
the antibody-coated beads are configured to attach to target cell-bound antigens in a biological sample added to the solution, the solution and the biological sample forming a mixture, and
when the container is positioned in the container holder such that the mixture is exposed to the magnetic field generated by the pair of magnets, bead-cell complexes formed between the antibody-coated beads and the target cell-bound antigens in the biological sample magnetically levitate within the container;
an imaging device coupled to the magnetic levitation apparatus and configured to capture at least one image of the bead-cell complexes in the mixture and to identify the target cell-bound antigens, when the mixture is present in the magnetic field of the magnetic levitation apparatus; and
a display configured to display information about the target cell-bound antigens in the mixture determined based, at least in part, on the at least one image captured by the imaging device.

18. The portable POC device of claim 17, further comprising a computer processor configured to process the at least one image captured by the imaging device to determine the information about the target cell-bound antigens in the mixture.

19. The portable POC device of claim 17, further comprising a network interface configured to:
send the at least one image captured by the imaging device to a remote computer processor configured to analyze the at least one image; and
receive, from the remote computer processor, the information about the target cell-bound antigens in the mixture.

20. The portable POC device of claim 17, wherein the information about the target cell-bound antigens in the mixture is selected from the group consisting of:
a levitation height of the bead-cell complexes in the mixture,
a presence or an absence of bead-cell complexes in the mixture, an antigen identification of one or more cell-bound antigens in the mixture, and
a concentration of one or more cell-bound antigens in the mixture.

\* \* \* \* \*